(12) United States Patent
Neera et al.

(10) Patent No.: US 7,485,462 B2
(45) Date of Patent: Feb. 3, 2009

(54) **COMMERCIALLY VIABLE PROCESS FOR IN-VITRO MASS CULTURE OF *CHLOROPHYTUM BORIVILIANUM***

(75) Inventors: Bhardwaj Neera, Gujarat (IN); K. S. Murali, Maharashtra (IN)

(73) Assignee: Reliance Life Sciences Pvt. Ltd., Rabale, Navi Mumbai, Maharashtra (IN)

( * ) Notice: Subject to any disclaimer, the term of this patent is extended or adjusted under 35 U.S.C. 154(b) by 478 days.

(21) Appl. No.: 11/095,161

(22) Filed: Sep. 29, 2005

(65) Prior Publication Data

US 2006/0015963 A1    Jan. 19, 2006

(30) Foreign Application Priority Data

Mar. 31, 2004  (IN) .......................... 398MUM/2004

(51) Int. Cl.
*C12Q 1/68* (2006.01)

(52) U.S. Cl. .................. 435/430.1; 435/420; 435/6

(58) Field of Classification Search .............. 435/430.1, 435/420, 6
See application file for complete search history.

(56) References Cited

U.S. PATENT DOCUMENTS

| | | | |
|---|---|---|---|
| 6,900,057 B2 * | 5/2005 | Burns et al. .............. 435/430.1 |
| 2004/0191780 A1 * | 9/2004 | Parvatam et al. ............... 435/6 |

* cited by examiner

*Primary Examiner*—Kent L Bell
(74) *Attorney, Agent, or Firm*—J. Harold Nissen; Lackenbach Siegel, LLP

(57) ABSTRACT

The present invention relates to the commercially viable process for in-vitro mass culture of *Chlorophytum borivilianum*. The present invention process for in-vitro mass culture of *Chlorophytum borivilianum* is simple, faster and suitable for production of disease free root tubers of uniform quality. The process of the present invention for in-vitro mass culture of *Chlorophytum borivilianum* employs media with low concentration of nutrients and phytohormones.

17 Claims, 2 Drawing Sheets

COMMERCIALLY VIABLE PROCESS FOR IN-VITRO MASS CULTURE OF CHLOROPHYTUM BORIVILIANUM

FIELD OF THE INVENTION

The present invention relates to the commercially viable process for in-vitro mass culture of *Chlorophytum borivilianum*. More particularly the present invention relates to the process for in-vitro mass culture of *Chlorophytum borivilianum* using media with low concentration of nutrients and phytohormones.

BACKGROUND OF THE INFORMATION

*Chlorophytum borivilianum* is a traditional medicinal plant in India, commonly known as Safed musali. It is partly a herb with sub-erect lanceolate leaves belonging to family *Liliaceae*, a family of 256 species distributed all over the world, with about 17 species found in India.

Predominantly *Chlorophytum borivilianum* is used as nutritive health tonic or health vitalizer especially for geriatric and general sexual weakness and also for motherhood where it is a curative for pre and postnatal problems as well as lactation enhancer. It is accepted as restorative for immunity improvement; hence it is also given for treating jaundice, gastro, and urinary track infection. Use of *Chlorophytum borivilianum* as a remedy for diabetes and arthritis has also been advocated. In Ayurvedic system of medicine, different preparations of *Chlorophytum borivilianum* are used for treatment of different symptoms or diseases. It is also a principal ingredient in many Unani and Tribal medicine mainly in Rajsthan and Gujarat. However the most popular use of *Chlorophytum borivilianum* roots is as Aphrodisiac and sex tonic for males Moreover now it is being considered a neutraceutical and efforts are as to make chips and flakes from *C. borivilianum* roots in some countries On account of its medicinal use in various disciplines like Ayurveda, Unani, and use in modern herbal products as well as its use by tribal healers, especially for its reputation as restorative tonic for males, there is a very vast demand for *Chlorophytum borivilianum* all over the world. To meet these huge demands there has been continuous ruthless depletion of *Chlorophytum borivilianum*. Although it was widely available in Indian forests demand is increasing rapidly in Indian and international drug markets. There is report for its foreign demand being estimated to be 300-700 tones annually, a quantity that Indian forests cannot support. In nature *Chlorophytum* is propagated through roots and roots are the medicinally useful part. Once the root is harvested from any place, the whole plant dies and reseeding never occurs at that place. Thus its depletion is much faster than the pace of its regeneration in nature.

*Chlorophytum borivilianum* is not under commercial cultivation as medicinal crop in any part of the world except in India. Due to ever-increasing requirement of *Chlorophytum borivilianum* and its high commercial value there have been attempts to in India to start commercial cultivation of *Chlorophytum borivilianum*. Cultivation by conventional propagation method is known to take long time for multiplication because of the low rate of fruit and seed set, poor seed germination and viability. It is reported that there is 8 months dormancy and seeds and germination percentage in the seeds of *C. borivilianum* is as low as 25-30 percent. Also often root and rhizome accumulate active ingredient only when they attain specific growth or development stage over a time. Furthermore the use of the root finger as means for propagating *Chlorophytum borivilianum*, as an alternate to seed would not be very good proposition since roots are the required organs for medicinal purpose.

However, the vegetative propagation through its fleshy roots is a very popular and easy method of commercial cultivation of *Chlorophytum borivilianum*. Two to five fingers along with the part of crown (depending on the length of finger) weighing between 8-15 gm is most suitable as planting material. Availability of the roots as a planting material at reasonable cost is one of the major problems of serious concern in large-scale multiplication of *Chlorophytum borivilianum*. Though there are some initiatives with respect to the commercial cultivation of *Chlorophytum borivilianum*, due to limited numbers of growers, the planting material is available at a very high cost which has made *Chlorophytum borivilianum*, very costly crop. There are also instances of many fungal species attacking this crop. The purchasers, that are new growers wanting to cultivate *C. borivilianum* unaware of these fungal infestations, buy and use these infested roots as planting material. Moreover in the name of the control, the farmers are reported to dip the infested roots in very high concentration of mercurial fungicide.

Besides high cost and poor availability of planting material, lack of technical information and proper market for the end produce are another restraint in large-scale cultivation of *C. borivilianum*.

Moreover, as per conventional cultivation practices, the *C. borivilianum* is a popular rainy season (kharif) crop in India and a commercial root harvest is obtained in 3-4 months. Thus limiting the cultivation of *C. borivilianum* only to specific period of the year that is monsoon, and thereby the fresh roots cannot be obtained round the year by such conventional cultivation methods. Moreover due to the uncertainty of rainfall, such rain dependant method of cultivation cannot always be relied upon for the market requirement.

Therefore, in view of the afore mentioned drawbacks associated with the conventional propagation methods, there exists a critical need for providing a method for Commercial propagation of *C. borivilianum* which is devoid of shortcoming of conventional cultivation, faster, and economical for large scale multiplication and can provide the planting material at an economical cost to the farmers.

Furthermore, due to the fact that there are more than 175 species of *Chlorophytum* reported in the world, they are used as ornamental plant, in India, it is treated as medicinal plant. There are about 13 species of Chlorophytum have been reported in India for example *C. arundinaceum, C. tuberosum, C. laxum, C. breviscapum* etc. All these species are totally different in medicinal properties but due to lack of correct information all species are known as Safed Musali in Indian drug market. In the reputed books of Ayurveda the plant mentioned as Safed Musali can be correlated only to *Chlorophytum borivilianum*.

Therefore in view of the above it is imperative to provide a means for in-vitro mass culture of *Chlorophytum borivilianum* for large-scale multiplication which is economical can also provide a reliable method specific to authentic Safed Musali that is correct species of *Chlorophytum* that is *C. borivilianum* and produce on the commercial scale the true to type clones of elite variety with disease free root tubers of uniform quality.

PRIOR ART

Dave A, et al "Micropropagation of Safed Musli (*Chlorophytum borivilianum*), a rare Indian Medicinal Herb", Plant Cell Tissue & Organ Culture, 39(10) 1994, describes in vitro clonal multiplication of safed musli (*Chlorophytum borivilianum* Sant et. Fernand.), by using shoot bases on MS medium supplemented with 22.2 mu M benzyladenine. Shoot multiplication is achieved four fold every three weeks and rooting is achieved on MS medium with three fourth strength MS medium with 9.8 mu M indolebutyric acid.

However the success rate of plant survival in the field (pots) is only 67%. Moreover the explant used is shoot bases and not isolated meristematic tissue hence the chances of getting true to type clone by this method can not be assured. Therefore the above mentioned method would not be very desirable for producing true to type clones of *C. borivilianum*.

In accordance with the present invention there is provideds a commercially viable process for in-vitro mass culture of *Chlorophytum borivilianum* for large-scale multiplication of the true to type clones of elite variety with disease free root tubers of uniform quality which can survive in the field at the rate of as much as about 100%.

OBJECTS OF THE INVENTION

Accordingly it is an object of the present invention to provide the commercially viable process for in-vitro mass culture of *Chlorophytum borivilianum* which is simple and faster, for production of the true to type clones of elite variety.

It is also an object of the present invention to provide a commercially viable process for in-vitro mass culture of *Chlorophytum borivilianum* which is suitable for commercial production of disease free root tubers of uniform quality.

SUMMARY OF THE INVENTION

There is provided a simple and faster commercially viable protocol for in-vitro mass culture of true to type clones of elite variety of *Chlorophytum borivilianum*.

In the most preferred embodiments of the present invention a commercially viable process for in-vitro mass culture of *Chlorophytum borivilianum* through organogenesis using media with low concentration of nutrients and phytohormones, in which broadly the process comprises of:

It is also an object of the invention to provide an identification of the best suitable explant with ability to give maximum regenerates.

Isolating explant from elite variety of mother plant; cleaning and sterilizing the explants by primary and secondary sterilization; inoculating the explants on hormone free culture initiation medium comprising of basal salts of MS medium to give multiple shoots;

transferring the cultures to proliferation and elongation medium comprising of basal salts of MS medium;

transferring the elongated shoots to hormone free rooting medium comprising of basal salts of MS medium;

subjecting in-vitro grown plantlets to primary and secondary hardening.

In preferred embodiments explants are selected from leaf, lateral roots, or crown meristem or the like. In the most preferred embodiments the explant is the crown meristem.

In the present invention the method for extraction of and surface sterilization of explants is provided such that it does not damage the isolated tissues.

In the most preferred embodiments of the present invention the MS medium employed for culture initiation, proliferation and elongation and rooting comprises of nutrient components in half the strength, thereby rendering the process cost-effective.

In the preferred embodiments the hardening process is so provided that the success rate regenerated plant is as much as upto 100% rate of survival in the field.

DEATAILED DESCRIPTION OF THE INVENTION

Figure 1:
FIG. 1—shows culture with multiple shoots from single explant.
Figure 2:
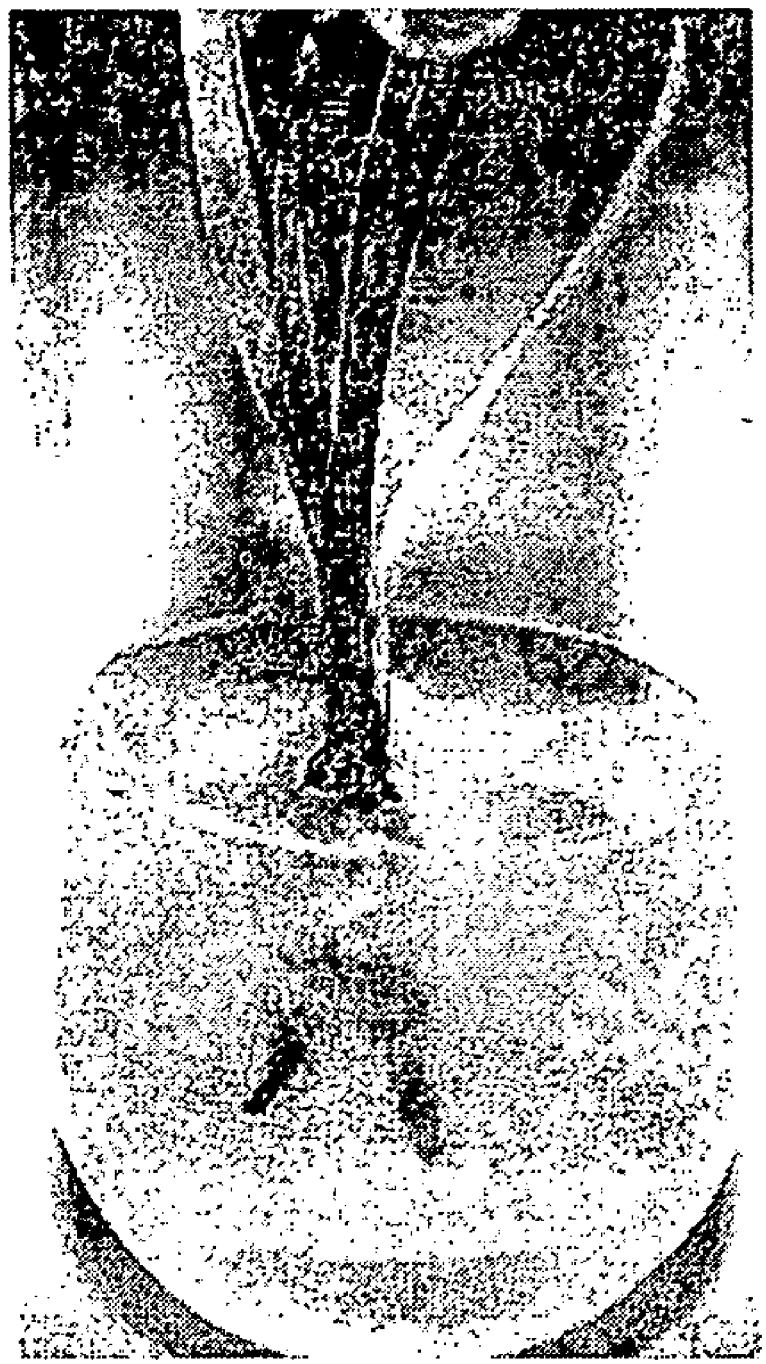
FIG. 2—shows single isolated shoot

The present invention provides a commercially viable process for in-vitro mass culture of *Chlorophytum borivilianum* for large-scale multiplication of the true to type clones of elite variety.

In accordance with the present invention there is provided a commercially viable process for in-vitro mass culture of *Chlorophytum borivilianum*, which is simple, and faster for production of disease free root tubers of uniform quality.

In accordance with the present invention there is provided a method for propagation of *C. borivilianum* through organogenesis for producing clones on commercial scale.

It is an important aspect of the present invention to identify the best suitable explant with ability to give higher number of regenerates.

It is an important aspect of the present invention to provide a standardized method for extraction of and surface sterilization of explants without damaging the isolated tissues.

In other aspect of the present invention there is provided the best suitable nutrient media supplemented with optimum growth regulators and other components required for different modes and phases of regeneration.

It is an important aspect of the present invention to provide the optimum growth conditions with respect to physical parameters like temperature, relative humidity, photoperiod and light intensity for all the stages of culture.

It is an important aspect of the present invention to provide the optimum sub-culture interval during in vitro culture.

It is also an additional aspect of the present invention to provide the hardening protocol for the regenerated plants with as much as about 100% rate of survival in the field.

In preferred embodiments of the present invention the process for in-vitro mass culture of *Chlorophytum borivilianum* for large-scale multiplication of the true to type clones of elite variety broadly comprises of:

isolating of explant from selected mother plants;

cleaning and sterilization of the explant;

inoculation of the explant on culture initiation medium to give multiple shoots;

transferring the cultures to proliferation and elongation medium;

transferring the elongated shoots to the rooting medium;

hardening of the in-vitro grown plants.

The hardened plants are then transferred to the field.

In preferred embodiments of the present invention for isolation of explants mother plants were selected and assessed for their root size, weight, general growth, appearance and absence of infection or contamination to decide requisite eliteness of the mother plant.

In the present invention the explant can be isolated from the mother plants growing in various locations, both wild and cultivated. Alternatively explant can also be isolated from selected elite mother plants grown in green house under controlled conditions to keep them disease free. To keep the mother plants disease free they can be subjected to decontamination pretreatment process comprising of spraying the mother plants regularly with agents like fungicides, insecticides, pesticides or the like. In the most preferred embodiments the mother plants are maintained at least for the periods of 15 to 20 days in the green house to reduce the rate of contamination during culture.

The fungicides for the pretreatment of the mother plant can be selected from the group comprising of Bavisitn, Captan, Dithane, Thiram, Thiovit or the like, and or combinations thereof at a concentration of about 0.05% to 0.2%.

Insecticide for the pretreatment of the mother plant can be selected from the group comprising of Rogor, Nuvacron, Fastac, Ultracid 40-WP, Thiodane or the like at a concentration of about 0.005% to 0.02%.

In preferred embodiments meristematic tissues are used as an explant. It is the meristematic tissue of a plant, which carries all the genetic information of mother plants. Moreover meristematic cells do not have alteration in DNA sequencing, which is found in the differentiated cells or tissues. Therefore the plants regenerated by using meristematic tissue as an explant produces the clones of selected elite variety. Explant used in the present invention can be selected from leaf, lateral root, crown meristem, or the like for initiation of culture. In the most preferred embodiments the contemplated explant is crown meristems.

The explant were cut from the healthy mother plant and subjected to cleaning and surface sterilization treatment prior to inoculation to culture media.

In accordance with the present invention for cleaning and surface sterilization of an explant various agents are employed like mild detergent, fungicide, bactericide, surface sterilizing agent, or the like and or combinations thereof.

In accordance with the present invention fungicide used for the surface sterilization of explant can be selected from group comprising of Bavisitn, Captan, Dithane, Thiram, Thiovit or the like, at a concentration of about 0.05% to 0.2%.

In accordance with the present invention bactericide used for the surface sterilization of explant can be selected from group comprising of streptomycin, chloramphenicol, ciprofloxacin, cefotaxime, kanamycin, carbenicillin, at a concentration of about 0.002% to 0.5%.

In accordance with the present invention fungicide used for the further surface sterilization of explant can be mercuric chloride at a concentration of about 0.05% to 0.5%.

In accordance with the present invention surface sterilizing agent used for the surface sterilization of explant can be selected from group comprising of sodium hypochlorite, calcium hypochlorite or the like at concentration of about 0.2% to 2%.

The present invention employs different explant than the ones reported previously to give large number of clones. The inventors of the present invention have for the first time provided the use of specifically isolated crown meristematic tissue as an explant for direct organogenesis giving rise to true to type clones. The success of the present invention depends upon the manner in which the explant is isolated prepared and sterilized.

In the most preferred embodiments of the present invention employing crown meristematic tissue as the explant the process for isolation, cleaning, sterilization and final preparation of explant comprises of: collecting the root of selected mother plant of *C. borivilianum*, washing thoroughly under running water to remove soil adhering to it, cutting approximately 1 to 2 cm pieces of root top with crown meristem, cleaning with mild detergent like 0.5 to 5% Tween-20 solution with intermittent shaking for 15 to 30 minutes, washing thoroughly with demineralized water; subjecting the cleaned explant to primary sterilization by treating the explants with a solution containing a fungicide like Bavistin 0.05% to 0.2% and a bactericide like streptomycin 0.1% to 1% for 20-80 minutes, rinsing with sterile water, cutting the crown part of tuberous roots about 0.5-1 cm below the apex and subjecting to secondary sterilization in a Laminar flow bench by treating with surface sterilizing agent like sodium hypochlorite 0.5-2% for 5 to 20 minutes, rinsing with autoclaved distilled water repeatedly, treating with fungicide like mercuric chloride 0.05 0 0.25% for 2 to 5 minutes, rinsing with sterile distilled water thrice; for final preparation of explant that is meristematic tissue for inoculation, trimming the explant to about 0.3 to 0.6 cm cube, without damaging the crown meristem, and taking care of isolating only the crown meristematic tissue and not other tissues. In accordance with the present invention, since the explant used that is root being sub-soil in nature, which is known to have tendency of heavy surface microbial presence, to avoid the contamination and resultant loss of valuable cultures each explant was washed and treated separately.

The sterilized explants were inoculated on culture initiation medium, and kept in suitable culture conditions to give multiple shoots. The multiple shoots were isolated and transferred onto proliferation and elongation medium and kept in growth room having predefined culture conditions favourable for the healthy development of the cultures. The elongated shoots can be subcultured at a regular interval. The healthy elongated shoots were transferred to rooting medium and allowed to grow to give well-formed roots. Plantlets were hardened on soil, sand, moss, charcoal or other media either alone or in combination in defined ratio.

The present invention employs various nutrient media for different phases like culture initiation medium, proliferation and elongation medium and rooting medium. The basal media for any of the afore-mentioned medium can be any of those already known in the field of the art like Murashige & Skoog, Gamborg's, Vacin & Went, White's, Schenk & Hildebrandt or the like, The basal media in accordance with the present invention can be supplemented with carbon source like sucrose or glucose or the like at concentration of about 2-5%, sugar alcohol like myo-inositol or the like at concentration of about 50-500 mg per liter, gelling agent like agar, alginic acid, carageenan, gellangum or the like at concentration of about 0.5-1%, further supplemented with phytohormones like natural or synthetic auxins, cytokinins, Gibberellin, or cytokinin-active urea derivatives, or the like depending on the requirement for a particular phase for which the medium is used.

In accordance with the present invention the natural and synthetic cytokinins used may be selected from the group consisting of 6-aminopurin (adenine), 6-aminopurine hydrochloride, 6-aminopurine hemisulfate, benzylaminopurine (BAP), kinetin, zeatin, n.sup.6-substituted derivatives or the like.

In accordance with the present invention the natural and synthetic auxin used may be selected from the group consisting of naphthalene acetic acid, naphthaleneacetamide, naphthoxyacetic acid, indole acetic acid, indole butyric acid, 4-Chlorophenoxyacetic acid, 2,4-Dichlorophenoxyacetic Acid (2,4-D), 2,4,5-Trichlorophenoxyacetic acid, or the like and their derivatives or the like.

Cytokinin-active urea derivatives may be selected from the group consisting of thiadiziron, diphenylurea, N-phenyl-N'-(4-pyridyl)urea or the like and their derivatives or the like.

In accordance with the present invention the growth regulator used in the nutrient media required at different stages may be single or combination of two or more of the above listed groups. Depending upon the type of the growth regulator selected, the amount thereof will vary. The growth regulators may be incorporated at a concentration of about form 0.01 mg per liter to 10 mg per liter.

In preferred embodiments of the present invention the culture medium for initiation, proliferation and elongation, and rooting is preferably Murashige & Skoog medium with half strength of the basal nutrients.

In preferred embodiments of the present invention the initiation medium is free of any phytohormones.

In preferred embodiments of the present invention the proliferation and shoot elongation medium comprises of cytokinine preferably 6-benzyl amino purine in the range of about 0.01 to about 0.9%, in the most preferred embodiments it is 0.05% to 0.5%.

In preferred embodiments the culture conditions for all stages of growth that is initiation, proliferation and elongation as well rooting were the same. The culture conditions were 16 hours photoperiod at about 2000 lux light intensity, followed by 8 hours of dark period, temperature was kept constant at 22° C. to 27 C and RH was maintained at about 70%.

In preferred embodiments elongated shoots are subcultured on proliferation and elongation medium at an interval of every 3 to 4 weeks.

The multiplication ratio obtained by method of the present invention is as high as 1:3 to 1:6.

The success rate during rooting was upto 100% and during hardening upto 90%. Thus it is evident that the method of the present invention has a very high success rate.

Thus the use of crown meristematic tissue as an explant; use of low strength of the basal salts in MS medium for different phases of culture, hormone free initiation medium and addition of very low concentrations of the plant growth regulator that is only 0.05% to 0.5% of 6-benzyl amino purine in proliferation and initiation medium giving give high number of multiple shoots in the range of 3-9 shoots per explant and high success rate during rooting and hardening renders the present invention process commercially viable for in-vitro mass culture of *Chlorophytum borivilianum* for large-scale multiplication of the true to type clones of elite variety.

Further features and aspects of the present invention are illustrated in following non-limiting example:

EXAMPLE

Example 1

The roots of healthy elite mother plant of *C. borivilianum* were collected. Roots were thoroughly washed under running water to remove soil adhering to it; approximately 1 to 2 cm pieces of root top with crown meristem were cut. Root pieces were separately cleaned with 5% Tween-20 solution with intermittent shaking for 15 minutes, washed thoroughly with demineralized water. Cleaned explants were subjected to primary sterilization by treating the explants with a solution containing a Bavistin 0.1% and streptomycin 0.25% for 20 minutes, rinsed with sterile water. The crown part of tuberous root about 1 cm below the apex was cut and subjected to secondary sterilization in a Laminar flow bench by treating with sodium hypochlorite 0.5% for 5 minutes, rinsing with autoclaved distilled water repeatedly, treating with mercuric chloride 0.1% for about 5 minutes, rinsing with sterile distilled water thrice. For final preparation of explant that is meristematic tissue for inoculation, the explant was trimmed about 0.5 cm cube, without damaging the crown meristem, and taking care of isolating only the crown meristematic tissue and not other tissues. To avoid the contamination and resultant loss of valuable cultures each explant was washed and treated separately.

The sterilized explants were inoculated on culture initiation medium comprising of half strength of Murashige & Skoog Basal Medium, and kept under initial photoperiod of 16 hours under 2000 lux light intensity followed by 8 hours dark period at 25° C. temperature and 75% RH to give multiple shoots. The multiple shoots ratio obtained was around 1:6. Shoots were isolated and transferred onto proliferation and elongation medium comprising of half strength of Murashige & Skoog Basal Medium with supplemented with 0.1 mg/lt of BA and kept in growth room having culture conditions same as defined above for initial multiplication stage. The elongated shoots were subcultured at a regular interval of about 4 weeks. The healthy elongated shoots were transferred to rooting medium comprising of half strength of Murashige & Skoog Basal Medium and allowed to grow to give well-formed roots. Plantlets were hardened and transferred to field.

We claim:

1. A commercially viable process for in-vitro mass culture of *Chlorophytum borivilianum* of true to type clone comprising the steps of:
   a. isolating meristematic explants from selected parts of a mother plant;
   b. cleaning the explants by washing thoroughly under running water to remove soil adhering to the explants, cutting approximately 1 to 2 cm pieces of root top with crown meristem, cleaning with a mild detergent of about 0.5 to 5% Tween-20 solution with intermittent shaking for a period of 15 to 30 minutes, and then washing thoroughly with demineralized water;
   c. subjecting the explants to a primary sterilization by treating the explants with a solution containing a fungicide comprising Bavistin at a concentration of 0.05% to 0.2% and a bactericide including streptomycin at a concentration of 0.1% to 1% for a period of 20-80 minutes, and then rinsing with sterile water;
   d. subjecting the primary sterilized explants to a secondary sterilization by cutting the crown part of tuberous roots about 0.5-1 cm below the apex in a Laminar flow bench, treating with a surface sterilizing agent comprising sodium hypochlorite in a range of 0.5-2% for a period of 0.05-0.25% for a period of 2 to 5 minutes, then rinsing with sterile distilled water thrice;
   e. preparing an explant that is a meristematic tissue for inoculation, by trimming the explant to about 0.3 to 0.6 cm cube, without damaging the crown meristem, and isolating the meristematic tissue;
   f. inoculating the explants on a culture initiation medium comprising basal salts of MS medium to give multiple shoots;
   g. transferring the cultures to a proliferation and elongation medium; and,
   h. transferring the elongated shoots to a rooting medium comprising basal salts of MS medium to produce said in vitro culture of *Chlorophytum borivilianum* of true to type clone.

2. The process as claimed in claim 1, wherein the MS medium used for culture initiation is of half strength.

3. The process as claimed in claim 1, wherein the culture initiation medium is a hormone free medium.

4. The process as claimed in claim 1, wherein the proliferation and elongation medium is supplemented with a low concentration of a phytohormone.

5. The process as claimed in claim 1, including phytohormone in the range of about 0.01 to about 0.9%.

6. The process as claimed in claim 1, wherein the MS medium used for rooting medium is of half strength.

7. The process as claimed in claim 1, wherein rooting medium is a hormone free medium.

8. The process as claimed in claim 4, wherein the phytohormone is 6-benzyl amino purine in the range of 0.05% to 0.5%.

9. The process as claimed in claim 1, wherein the proliferation and elongation medium is basal salts of MS medium.

10. The process as claimed in claim 1, wherein the fungicide is selected from the group consisting of Bavistin, Captan, Dithane, Thiram, and Thiovit.

11. The process as claimed in claim 1, wherein the bactericide is selected from the group consisting of streptomycin, chloramphenicol, ciprofloxacin, cefotaume, kanamycin and carbenicillin.

12. The process as claimed in claim 1, wherein the surface sterilizing agent is selected from the group consisting of sodium hypochlorite and calcium hypochlorite in a concentration between 0.2% to 2.0%.

13. The process as claimed in claim 1, including phytohormone selected from the group consisting of natural and synthetic auxins, cytohinins, Gibberellin and cytokinin-active urea derivatives.

14. The process as claimed in claim 1, including natural and synthetic cytokinins selected from the group consisting of 6-aminopurin (adenine), 6-aminopurine hydrochloride, 6-aminopurine hemisulfate, benzylaminopurine (BAP), kinetin, zeating and n.sup 6-substituted derivatives.

15. The process as claimed in claim 4, wherein the phytohormone is 6-benzyl amino purine in the range of about 0.01 to about 0.9%.

16. A commercially viable process for in-vitro mass culture of *Chlorophytum borivilianum* of true to type clone comprising the steps of:

a. isolating meristematic explants from leaf, lateral roots, or crown meristem of a mother plant;

b. cleaning the explants by washing through under running water to removal soil adhering to the explants, cutting approximately to 1 to 2 cm pieces of root top, cleaning with a 0.5 to 5% Tween-20 solution with intermittent shaking for a period 15 to 30 minutes, then washing thoroughly with demineralized water;

c. subjecting the explants to primary sterilization by treating the explants with a solution containing 0.05% to 0.2% Bavistin and 0.1% to 1% of streptomycin for 20-80 minutes, then rinsing with sterile water;

d. subjecting the primary sterilized explants to secondary sterilization by cutting the crown part of tuberous roots about 0.5-1 cm below the apex in a Laminar flow bench, treating with 0.5-2% of sodium hypochlorite for a period of 5 to 20 minutes, then rinsing with autoclaved distilled water repeatedly, treating with 0.05-0.25% of mercuric chloride for 2 to 5 minutes, then rinsing with sterile distilled water thrice;

e. preparing the explant that is meristematic tissue for inoculation, by trimming the explant to a cube of about 0.3 to 0.6 cm, without damaging the crown meristem, and taking care of isolating the meristematic tissue;

f. inoculating the explants with a medium of basal salts to produce multiple shoots;

g. transferring the cultures to a medium of basal salts of MS medium to produce a proliferation and elongation medium; and h. transferring the elongated shoots to a medium of basal salts of MS medium to provide for a rooting medium.

17. The process as claimed in claim 16, wherein crown meristem is the preferred explant.

* * * * *